United States Patent [19]

Saltzman

[11] 3,954,562

[45] May 4, 1976

[54] SYNTHESIS OF STEROIDS
[75] Inventor: William H. Saltzman, New Rochelle, N.Y.
[73] Assignee: Intellectual Property Development Corporation, New Rochelle, N.Y.
[22] Filed: Feb. 14, 1975
[21] Appl. No.: 550,082

[52] U.S. Cl. .............................................. 195/51 S
[51] Int. Cl.² ......................................... C12D 13/02
[58] Field of Search ......................... 195/51 R, 51 S

[56] References Cited
OTHER PUBLICATIONS

Aries et al., Biochimica et Biophysica ACTA, Vol. 202, pp. 535–543, (1970).

*Primary Examiner*—Alvin E. Tanenholtz

[57] ABSTRACT

A method of producing 12-dihydro steroids which comprises subjecting a 12-hydroxy steroid to the action of a 12-dehydroxylase producing microorganism.

5 Claims, No Drawings

SYNTHESIS OF STEROIDS

This invention relates to and has as its objective, the method of production of a 12-dihydro steroids which comprises subjecting a 12-hydroxy steroid to the action of a 12-dehydroxylase producing microorganism.

More particularly, this invention relates to a method for producing compounds of the formula

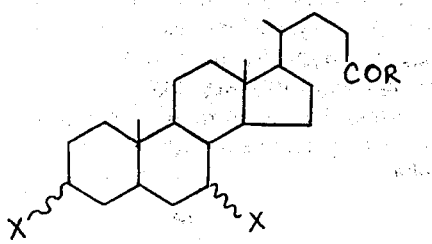

wherein each X is selected from the group consisting of hydrogen, hydroxy, acyloxy, alkoxy and oxo (O=); and R is selected from the group consisting of hydroxy, acyloxy, alkoxy, taurine and glycine; which comprises subjecting a compound of the formula

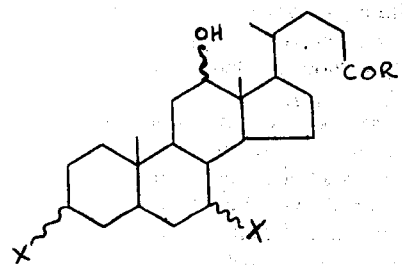

wherein X and R are as defined above, to the action of a 12-dehydroxylase producing microorganism of the group consisting of Clostridium and Bifidobacterium. Most preferably in the practice of this invention, each X is hydroxy, and R may be hydroxy, taurine or glycine. (Whenever, in the Specification and Claims of this application, a curved line ( $\xi$ ) is employed in the structural formulae set forth therein, it is meant to denote that the attached substituent may be in either the $\alpha$- or $\beta$-position, as the case may be.)

In the preferred practice of this invention, the final products produced thereby are the 3,7-disubstituted steroids and may include such compounds as $3\alpha, 7\alpha$-dihydroxy-$5\beta$-cholanic acid, and the taurine and glycine derivatives thereof, $3\alpha, 7\beta$-dihydroxy-$5\beta$-cholanic acid, and the taurine and glycine derivatives thereof; $3\alpha, 7\alpha$-diacyloxy-$5\beta$-cholanic acid, 3,7-dioxo-$5\beta$-cholanic acid, and $3\alpha, 7\alpha$-dialkoxy-$5\beta$-cholanic acid, and derivatives thereof, all of which are known compounds, and some of which have desirable pharmacological properties, for example, hypolipidemic activity.

Among the preferred 12-hydroxy substituted starting materials which may be satisfactorily employed in the practice of this invention, may be included such compounds as 3, 7, 12,-trihydroxy-$5\beta$-cholanic acid, and its alkoxy, acyloxy, taurine and glycine derivatives; for example $3\alpha, 7\alpha, 12\alpha$-trihydroxy-$5\beta$-cholanic acid; $3\alpha, 7\beta, 12\alpha$-trihydroxy-$5\beta$-cholanic acid, and other such 12-hydroxylated starting materials.

The preferred acyloxy radicals of this invention are those derived from hydrocarbon carboxylic acids of less than 12 carbon atoms, and include such acids as the alkanoic acids, alkenoic acids, aryl carboxylic acids, cycloalkanoic acids, and cycloalkenoic acids.

The preferred alkoxy radicals of this invention are those derived from lower alkyl moieties of 6 carbon atoms or less, and include such alkoxy groups as methoxy, ethoxy, butoxy and the like.

In order to produce the final compounds of the instant invention, the 12-hydroxylated starting material is subjected to the action of a 12-dehydroxylase producing microorganism of the group consisting of Clostridium and Bifidobacterium. More particularly, the 12-hydroxylated starting materials may be subjected to the action of the dehydroxylase enzyme of the desired microorganism, or directly to the action of the microorganism itself under the proper conditions and in the necessary medium in which the microorganism can be propagated. Depending upon the nature of the 12-dehydroxylase producing microorganism itself, the microorganism and the medium in which it may be grown may be varied to accommodate the specific microorganism involved, and may be modified depending upon the results desired or the microorganism employed.

Among the microorganisms which may be employed in the practice of this invention may be generally included those 12-dehydroxylase producing microorganisms and more particularly those of the genera Clostridium and Bifidobacterium. More particularly, the 12-dehydroxylase enzyme producing microorganisms which may be employed include such microorganisms as *Clostridium perfringens*, for example, *Clostridium perfringens* (ATCC-19574), and *Clostridium welchii*. In addition, those 12-dehydroxylase producing microorganisms of the genus Bifidobacterium may also be employed.

In general, the conditions of culturing the desired microorganisms for the purpose of this invention are, except for the inclusion of the 12-hydroxylated starting material, the same as those employed in the culturing of like organisms for such purpose, i.e., the microorganism is grown, either aerobically or anaerobically (depending on the microorganism chosen, for example, Clostridia are generally cultured under anaerobic conditions) in contact with (in or on) a suitable fermentation medium. A suitable medium essentially comprises a source of carbon and energy. The latter may be a carbohydrate, a fatty acid, a fat and/or the 12-hydroxylated steroid material itself. Among the fats utilizable are lard oil, soybean oil, linseed oil, etc. Among the fatty acids are stearic acid palmetic acid and the like. The source of nitrogenous factors may be organic (e.g., soybean meal, corn steep liquor and/or distiller's solubles) or synthetic, composed of synthesizable organic or inorganic compounds such as ammonium salts, alkali nitrates, amino acids, urea).

For aerobic fermentation, an adequate sterile air supply should be maintained. For anaerobic fermentation, external sources of oxygen should be excluded from the fermentation vessels. The 12-hydroxylated starting material may be added to the culture during the incubation period, or included in the medium prior to sterilization or inoculation. A satisfactory (but not limiting) range of concentration of the 12-hydroxylated steroid starting material, for example, $3\alpha, 7\alpha, 12\alpha$-trihydroxy-$5\beta$-cholanic acid in the culture can be about 0.01 to about 0.5%, however, this concentration may be increased depending upon the ability of the microorganism to properly grow in the resultant media. The culture period, or rather the time of subjecting the 12-hydroxylated steroid starting material to the action of the 12-hydroxylase enzyme, may vary considerably, the range of 4 to 96 hours being feasible but not limiting. In addition, the pH of the culture medium may be varied from about 5.0 to about 7.0, without effecting the final results obtained.

The following Example is illustrative of the invention:

EXAMPLE 1

To 50 ml. of a medium comprising Brewer modified throgylcollate broth (Baltimore Biological Laboratories), a stock culture of *Clostridium perfringens* ATCC 19574 is inoculated under anaerobic conditions. The medium is incubated under anaerobic conditions, at 37° C for a period of 96 hours and the resultant culture is employed to inoculate 1 liter of the same medium. At the time of inoculation, 2 gm. of 3$\alpha$, 7$\alpha$, 12$\alpha$-trihydroxy-5$\beta$-cholanic acid dissolved in 15 ml. of ethenol and sterilized through a Seitz pad is added. The flask is incubated anaerobically for 72 hours and the broth is then filtered on a Buchner funnel with the aid of filter cel and the filtrate is then acidified to pH 1–2 with HCl, extracted 3 times with ether and the combined ether extracts washed with water, dried over sodium sulfate, and evaporated to dryness in vacuo. The residue is then crystalized from ethyl acetate-heptane to yield crude 3$\alpha$, 7$\alpha$,-dihydroxy-5$\beta$-cholanic acid. If further purification is required, the resultant product may be further treated in accordance with the procedures set forth in my copending application, Ser. No. 417,170, filed Nov. 19, 1973.

The invention may be variously otherwise encompassed within the scope of the appended claims.

What is claimed is:

1. The method of producing a compound of the formula:

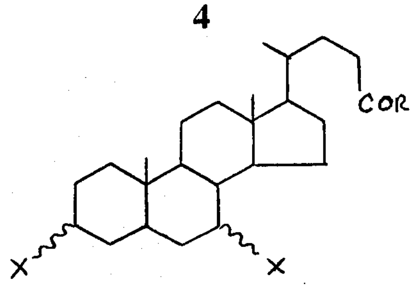

wherein each X is selected from the group consisting of hydrogen, hydroxy, acyloxy, alkoxy and oxo (O=), and R is selected from the group consisting of hydroxy, acyloxy, alkoxy, taurine and glycine, which comprises:

a. subjecting a compound of the formula 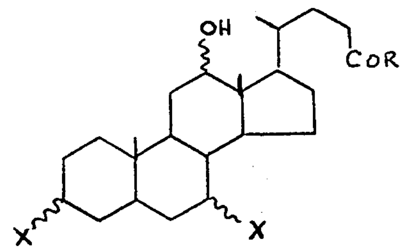 wherein X and R are as defined above, to the action of a 12-dehydroxylase enzyme produced by a clostridium perfringen microorganism in a suitable medium; and recovering the said final product.

2. The method of claim 1, wherein each X is $\alpha$-hydroxy.

3. The method of claim 1, wherein the compound of step (a) is 3$\alpha$, 7$\alpha$, 12$\alpha$,-trihydroxy-5$\beta$-cholanic acid.

4. The method of claim 1, wherein the final product is 3$\alpha$, 7$\alpha$-dihydroxy-5$\beta$-cholanic acid.

5. The method of claim 1, wherein the compound of step a. is 3$\alpha$, 7$\alpha$, 12$\alpha$-trihydroxy-5$\beta$-cholanic acid, and the final product is 3$\alpha$, 7$\alpha$-dihydroxy-5$\beta$-cholanic acid.

* * * * *